United States Patent

Perronnet et al.

[11] 4,000,267
[45] Dec. 28, 1976

[54] INSECTICIDAL AND ACARICIDAL COMPOSITONS EMPLOYING PYRIDO [1,2a]pyrimidinone thiophosphates

[75] Inventors: Jacques Perronnet, Paris; Laurent Taliani, Les Pavillons Sous Bois, both of France

[73] Assignee: Roussel-UCLAF, Paris, France

[22] Filed: June 23, 1975

[21] Appl. No.: 589,466

Related U.S. Application Data

[62] Division of Ser. No. 394,078, Sept. 4, 1973, Pat. No. 3,904,624.

[30] Foreign Application Priority Data

Sept. 11, 1972 France .............................. 72.32088.

[52] U.S. Cl. ............................................. 424/200
[51] Int. Cl.² ......................................... A01N 9/36
[58] Field of Search ................. 424/200; 260/251 P

[56] References Cited

FOREIGN PATENTS OR APPLICATIONS 2,152,469    4/1973    France
2,245,386    3/1973    Germany Primary Examiner—Jerome D. Goldberg
Assistant Examiner—Allen J. Robinson
Attorney, Agent, or Firm—Hammond & Littell

[57] ABSTRACT

Novel insecticidal and acaridicidal compositions containing organo-phosphorus compounds of the formula

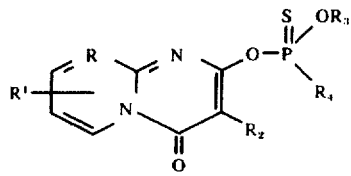

wherein R is selected from the group consisting of methine and nitrogen, $R^1$ is selected from the group consisting of hydrogen, alkyl of 1 to 3 carbon atoms and $NO_2$, $R_2$ is selected from the group consisting of hydrogen, straight or branched alkyl of 1 to 3 carbon atoms, chlorine, bromine, alkoxycarbonyl of 2 to 4 carbon atoms, phenyl and thioalkyl of 1 to 4 carbon atoms, $R_3$ is branched or straight chain alkyl of 1 to 3 carbon atoms and $R_4$ is selected from the group consisting of straight and branched chain alkyl of 1 to 3 carbon atoms, alkoxy of 1 to 3 carbon atoms and

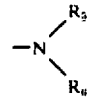

wherein $R_5$ and $R_6$ are individually selected from the group consisting of hydrogen and branched and straight chain alkyl of 1 to 3 carbon atoms.

6 Claims, No Drawings

INSECTICIDAL AND ACARICIDAL COMPOSITONS EMPLOYING PYRIDO 1,2a pyrimidione thiophosphates

PRIOR APPLICATION

This application is a division of our copending, commonly assigned application Ser. No. 394,078 filed Sept. 4, 1973, now U.S. Pat. No. 3,904,624.

OBJECTS OF THE INVENTION

It is an object of the invention to provide the novel organo-phosphorus compounds of formula I and to a novel process for their preparation.

It is another object of the invention to provide novel pesticidal compositions.

It is a further object of the invention to provide novel methods of combatting insects, nematodes and acarids.

These and other objects and advantages of the invention will become obvious from the following detailed description.

THE INVENTION

The novel organo-phosphorus compounds of the invention have the formula

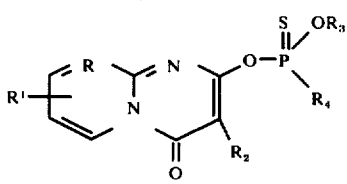

wherein R is selected from the group consisting of methine and nitrogen, $R^1$ is selected from the group consisting of hydrogen, alkyl of 1 to 3 carbon atoms and $NO_2$, $R_2$ is selected from the group consisting of hydrogen, straight or branched alkyl of 1 to 3 carbon atoms, chlorine, bromine, alkoxycarbonyl of 2 to 4 carbon atoms, phenyl and thioalkyl of 1 to 4 carbon atoms, $R_3$ is branched or straight chain alkyl of 1 to 3 carbon atoms and $R_4$ is selected from the group consisting of straight and branched chain alkyl of 1 to 3 carbon atoms, alkoxy of 1 to 3 carbon atoms and

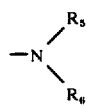

wherein $R_5$ and $R_6$ are individually selected from the group consisting of hydrogen and branched and straight chain alkyl of 1 to 3 carbon atoms.

Among the preferred compounds of formula I are those wherein $R^1$ is $R_1$ which is selected from the group consisting of hydrogen and alkyl of 1 to 3 carbon atoms. Preferably, alkyl is methyl or ethyl and alkoxy is methoxy or ethoxy.

The novel process of the invention for the preparation of compounds of formula I comprises reacting a compound of the formula

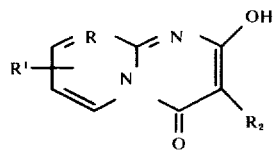

wherein R, $R^1$ and $R_2$ have the above definitions with a halogeno phosphate of the formula

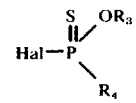

wherein $R_3$ and $R_4$ have the above definitions and Hal is chlorine or bromine in the presence of a hydrogen halide acceptor to form the corresponding compound of formula I.

The reaction is preferably effected in an organic solvent such as acetone, ethyl acetate or acetonitrile and Hal is chlorine and the acid acceptor may be potassium carbonate, triethylamine or pyridine, for example.

The starting material of formula II may be prepared by condensation of a 2-amino-pyridine or 2-amino-pyrimidine, optionally substituted, with an optionally substituted aryl or alkyl malonate. The compounds of formula II wherein $R_2$ is chlorine or bromine can be prepared by reacting the corresponding compound of formula II wherein $R_2$ is hydrogen with N-chloro- or N-bromo-succinimide. The compounds of formula II wherein $R_2$ is alkoxycarbonyl may be prepared by reacting a trisalkoxycarbonylmethane with an optionally substituted aminopyridine or aminopyrimidine.

The novel pesticidal compositions of the invention are comprised of an effective amount of at least one compound of formula I and a carrier. The compositions may also contain one or more other pesticidal agents and may be in the form of powders, granules, suspensions, emulsions or solutions containing the active ingredient in admixture, for example, with a vehicle and/or cationic, anionic or non-ionic surface active agent to ensure a uniform dispersion of the substances in the composition. The vehicle may be a liquid such as water, alcohol, hydrocarbons or other organic solvents, a mineral, vegetable or animal oil or a powder such as talc, clays, silicates or kieselguhr. The liquid compositions preferably contain 5 to 95% by weight of the active ingredient.

An example of an insecticidal composition of the invention is an emulsifiable concentrate consisting of 15% by weight of 2-(dimethoxythiophosphoryloxy)-pyrido [2,1a]-pyrimidine-4-one, 6.4% by weight of Atlox 4851 (oxyethylene triglyceride with a sulfonate having an acid No. of 1.5), 3.2% by weight of Atlox 4855 (oxyethylene triglyceride with a sulfonate having an acid No. of 3) and 75.4% by weight of xylene.

The compositions are useful as insecticides, acaricides and nematocides. Tests have shown them to be useful to combat insects such as *Aphis fabae*, *Prodenia litura*, *Musca domestica*, *Drosophila melanogaster*, *Blabera germanica*, *Sitophilus granarius*, *Tribolium confusum*, *Carpocapsa pomonella* and *Ceratitis capitata*, to combat nematodes such as Meloidogyn and to combat acarids such as *Tetranychus urticae*.

The novel method of the invention for combatting acarids, insects or nematodes comprises contacting insects, nematodes and/or acarids with a lethal amount of at least one compound of formula I.

In the following examples there are described several preferred embodiments to illustrate the invention. However, it should be understood that the invention is not intended to be limited to the specific embodiments.

EXAMPLE 1

2-(diethoxythiophosphoryloxy)-pyrido-[1,2a]-pyrimidine-4-one

A suspension of 40 g of 2-hydroxy-pyrido[1,2a]-pyrimidine-4-one [Ber., Vol. 57 (1924), p. 1168], 34 g of potassium carbonate in 400 ml of acetone and 39 ml of diethyl chlorothiophosphate was stirred at room temperature for 16 hours and was then refluxed for 5 hours. After removal of mineral salts, the mixture was evaporated to dryness. The oil residue was chromatographed over silica gel and a 1-1-1 cyclohexane-acetone-chloroform mixture was the eluant. Evaporation of the eluant resulted in 19 g of 2-(diethoxythiophosphoryloxy)-pyrido [1,2a]-pyrimidine-4-one in the form of white crystals melting at 82° C.

Analysis: $C_{12}H_{15}N_2O_4PS$

|  |  | %H 4.81 | %N 8.91 | %P 9.85 |
|---|---|---|---|---|
| Calculated: | %C 45.86 | %H 4.81 | %N 8.91 | %P 9.85 |
| Found: | 46.0 | 4.8 | 8.7 | 10.1 |

EXAMPLE 2

2-(dimethoxythiophosphoryloxy)-pyrido [1,2a]-pyrimidine-4-one

A mixture of 60 g of 2-hydroxy-pyrido [1,2a]-pyrimidine-4-one and 52 g of potassium carbonate in 1000 ml of acetone was refluxed for 30 minutes and then 46 ml of 0,0-dimethyl chlorothiophosphate were rapidly introduced after which reflux was continued for 4 hours. After cooling, the mixture was vacuum filtered to remove mineral salts and the filtrate was evaporated to dryness. The resulting red oil was added to 300 ml of ice water and the mixture was vacuum filtered. The precipitate obtained was washed with methanol, dried and dissolved in chloroform. The solution was filtered over magnesium silicate and evaporated to dryness to obtain 9.5 g of 2-(dimethoxythiophosphoryloxy)-pyrido [1,2a]-pyrimidine-4-one in the form of white crystals melting at 125° C.

Analysis: $C_{10}H_{11}N_2O_4PS$

| Calculated: | %C 41.96 | %H 3.88 | %N 9.78 | %P 10.82 |
|---|---|---|---|---|
| Found: | 41.9 | 4.1 | 9.6 | 11.0 |

EXAMPLE 3

2-(N-methyl-0-ethylthiophosphoramidoxy)-pyrido [1,2a]-pyrimidine-4-one

A mixture of 12 g of 2-hydroxy-pyrido [1,2a]-pyrimidine-4-one and 10.3 g of potassium carbonate in 500 ml of acetone was stirred at room temperature for 30 minutes and after the addition of 13 g of ethyl N-methyl chlorothiophosphoramidate [Chem. Ab., Vol. 60 (1964), p. 2828$_e$] thereto, the mixture was refluxed for 24 hours. The precipitate formed was vacuum filtered off and the filtrate was concentrated. The mixture was chromatographed over silica gel with a 1-1-1 chloroform-acetone-cyclohexane mixture as the eluant. Evaporation of the eluant resulted in 1.5 g of 2-(N-methyl-0-ethylthiophosphoramidoxy)-pyrido [1,2a]-pyrimidine-4-one as a cream-colored crystalline solid melting at 95° C.

Analysis: $C_{11}H_{13}N_3O_3PS$

| Calculated: | %C 44.29 | %H 4.39 | %N 14.09 | %P 10.38 |
|---|---|---|---|---|
| Found: | 44.2 | 4.8 | 13.8 | 10.3 |

EXAMPLE 4

2-(diethoxythiophosphoryloxy)-8-methyl-pyrido [1,2a]-pyrimidine-4-one

A mixture of 17.6 g of 2-hydroxy-8-methyl-pyrido [1,2a]-pyrimidine-4-one [J. Helv. Chem., Vol. 1 (1967), p. 523] and 13.8 g of potassium carbonate in 400 ml of acetone was stirred for 30 minutes at room temperature and after the addition of 18.8 g of 0,0-diethyl chlorothiophosphate, the mixture was stirred for 24 hours at room temperature. The mixture was vacuum filtered to remove mineral salts and the filtrate was concentrated. The resulting oil was chromatographed over silica gel using a 1-1-1 chloroform-acetonecyclohexane mixture as the eluant. Evaporation of the eluant resulted in an oil which was crystallized from hexane. The mixture was vacuum filtered to obtain 11.8 g of 2-(diethoxythiophosphoryloxy)-8-methyl-pyrido [1,2a]-pyrimidine-4-one in the form of clear yellow crystals melting at 75° C.

Analysis: $C_{13}H_{17}N_2O_4PS$

| Calculated: | %C 47.56 | %H 5.22 | %N 8.53 | %P 9.43 |
|---|---|---|---|---|

| Analysis: $C_{13}H_{17}N_2O_4PS$ | | | |
|---|---|---|---|
| Found: | 47.5 | 5.1 | 8.3 | 9.5 |

EXAMPLE 5

2-(dimethoxythiophosphoryloxy)-8-methyl-pyrido[1,2a]-pyrimidine-4-one

A mixture of 17.6 g of 2-hydroxy-8-methyl-pyrido[1,2a]-pyrimidine-4-one and 13.6 g of potassium carbonate in 400 ml of acetone was stirred at room temperature for 30 minutes and after the addition of 16 g of 0,0-dimethyl chlorothiophosphate, the mixture was stirred for 24 hours at room temperature. The mixture was vacuum filtered to remove mineral salts and the filtrate was concentrated. The residue was chromatographed over silica gel using a 1-1-1 chloroform-acetone-cyclohexane mixture as eluant. Evaporation of the eluant gave 6.2 g of 2-(dimethoxythiophosphoryloxy)-8-methyl-pyrido [1,2a]-pyrimidine-4-one in the form of yellow crystals melting at 110° C.

| Analysis: $C_{11}H_{13}N_2O_4PS$ | | | | |
|---|---|---|---|---|
| Calculated: | %C 44.00 | %H 4.36 | %N 9.33 | %P 10.31 |
| Found: | 44.0 | 4.4 | 9.0 | 10.3 |

EXAMPLE 6

2-(diethoxy thiophosphoryloxy)-pyrimido[1,2a]-pyrimidine-4-one

A mixture of 815 mg of 2-hydroxy-pyrimido [1,2a]-pyrimidine-4-one [Montashefte Chem., Vol. 93 (1962), p. 34] and 690 mg of potassium carbonate in 8 ml of acetone was stirred for 5 minutes and after the addition of 940 mg of diethyl chlorothiophosphate, the mixture was stirred overnight at room temperature. The mixture was then refluxed for 2 hours and filtered. The filtrate was evaporated to dryness to obtain 600 mg of a yellow oil. The oil was chromatographed over silica gel using as the eluant a 1-1-1 chloroform-acetone-cyclohexane. The eluant was evaporated to obtain 58 mg of 2-(diethoxythiophosphoryloxy)-pyrimido [1,2a]-pyrimidine-4-one in the form of a yellow oil.

| Analysis: $C_{11}H_{14}N_3O_4PS$ | | | | |
|---|---|---|---|---|
| Calculated: | %C 41.90 | %H 4.48 | %N 13.33 | %P 9.82 |
| Found: | 42.1 | 4.7 | 13.0 | 9.6 |

EXAMPLE 7

2-(diethoxythiophosphoryloxy)-3-methyl-pyrido[1,2a]-pyrimidine-4-one

A mixture of 35 g of 2-hydroxy-3-methyl-pyrido [1,2a]-pyrimidine-4-one [Ber., Vol. 57 (1924), p. 1168], 27 g of potassium carbonate and 31 g of diethyl chlorothiophosphate in 350 ml of acetone was stirred for 16 hours at room temperature and the mixture was filtered. The filtrate was evaporated to dryness to obtain a red oil which was chromatographed over silica gel using as eluant a 3-7 cyclohexane-ethyl acetate mixture. Evaporation of the eluant gave 5 g of 2-(diethoxythiophosphoryloxy)-3-methyl-pyrido [1,2a]-pyrimidine-4-one as yellow crystals melting at 78°–80° C.

| Analysis: $C_{13}H_{17}N_2O_4PS$ | | | | |
|---|---|---|---|---|
| Calculated: | %C 47.56 | %H 5.22 | %N 8.53 | %P 9.43 |
| Found: | 47.7 | 5.4 | 8.5 | 9.2 |

EXAMPLE 8

2-(diethoxythiophosphoryloxy)-3-carbethoxy-pyrido [1,2a]-pyrimidine-4-one

STEP A; 2-hydroxy-3-carbethoxy-pyrido [1,2a]-pyrimidine-4-one

A mixture of 9.4 g of 2-amino-pyridine and 23.2 g of tricarbethoxymethane was heated at 200° C until the distillation of ethanol ceased and after cooling, the residue was taken up in acetone. The resulting crystals were recovered by vacuum filtration to obtain 15.5 g of 2-hydroxy-3-carbethoxy-pyrido [1,2a]-pyrimidine-4-one melting at 198° C.

| I.R. Spectrum: | |
|---|---|
| $1712^{cm-1}$ | C=O |
| $1680^{cm-1}$ | C=O of conjugated ester |
| $1636^{cm-1}$ | C=C conjugated |

STEP B:

2-(diethoxythiophosphoryloxy)-3-carbethoxy-pyrido [1,2a]-pyrimidine-4-one

A mixture of 11.5 g of the product of Step A, 9.4 g of diethyl chlorothiophosphate and 7 g of potassium carbonate in 115 ml of acetone was stirred for 16 hours at room temperature and then was refluxed for 3 hours and cooled. The mixture was filtered and the filtrate was evaporated to dryness. The oil residue was chromatographed over silica gel using a 2–8 mixture of cyclohexane-ethyl acetate as eluant. Evaporation of the eluant resulted in 5 g of 2-(diethoxythiophosphoryloxy)-3-carbethoxy-pyrido [1,2a]-pyrimidine-4-one as yellow crystals melting at 105° C.

| Analysis: $C_{15}H_{19}N_2O_6PS$ | | | | |
|---|---|---|---|---|
| Calculated: | %C 46.63 | %H 4.96 | %N 7.25 | %P 8.01 |
| Found: | 46.7 | 5.0 | 7.3 | 7.9 |

EXAMPLE 9

2-(diethoxythiophosphoryloxy)-3-chloro-pyrido [1,2a]-pyrimidine-4-one

STEP A: 3-chloro-2-hydroxy-pyrido [1,2a]-pyrimidine-4-one

A suspension of 45 g of 2-hydroxy-pyrido [1,2a]-pyrimidine-4-one and 37 g of N-chloro-succinimide in 300 ml of acetic acid was refluxed for 5 hours and vacuum filtered hot. The solid recovered was rinsed with ether to obtain 47 g of 3-chloro-2-hydroxy-pyrido [1,2a]-pyrimidine-4-one as white crystals melting at 325° C.

STEP B: 2-(diethoxythiophosphoryloxy)-3-chloro-pyrido[1,2a]-pyrimidine-4-one A mixture of 30 g of the product of Step A, 24 ml of diethyl chlorothiophosphate, 21.4 ml of triethylamine and 400 ml of acetonitrile was stirred for 16 hours at room temperature and was then filtered. The filtrate was evaporated to dryness and the resulting crystals were taken up in a benzene-water mixture. The organic phase was separated, dried over sodium sulfate and evaporated to dryness. The product was crystallized from 300 ml of an 8–2 isopropyl ether-benzene mixture to obtain 19 g of 2-(diethoxythiophosphoryloxy)-3-chloro-pyrido [1,2a]-pyrimidine-4-one as white crystals melting at 130° C.

| Analysis: $C_{12}H_{14}ClN_2O_4PS$ | | | | | |
|---|---|---|---|---|---|
| Calculated: | %C 41.32 | %H 4.05 | %N 8.04 | %Cl 10.17 | %P 8.89 |
| Found: | 41.7 | 4.1 | 8.0 | 10.3 | 8.9 |

EXAMPLE 10

2-(diethoxythiophosphoryloxy)-7-nitro-pyrido [1,2a]-pyrimidine-4-one

STEP A: 2-hydroxy-7-nitro-pyrido [1,2a]-pyrimidine-4-one

A stirred mixture of 2.8 g of 2-amino-5-nitro-pyrimidine and 10 g. of trichlorophenyl malonate was heated at 230° C for 15 minutes and cooled to 50° C at which time 40 ml of acetone were added thereto. After cooling to room temperature, the mixture was vacuum filtered to obtain 3.2 g of 2-hydroxy-7-nitro-pyrido [1,2a]-pyrimidine-4-one as brown crystals melting at 320° C with decomposition.

| Analysis: $C_8H_5N_3O_4$ | | | |
|---|---|---|---|
| Calculated: | %C 46.35 | %H 2.43 | %N 20.28 |
| Found: | 46.4 | 2.3 | 19.9 |

STEP B: 2-(diethoxythiophosphoryloxy)-7-nitro-pyrido [1,2a]-pyrimidine-4-one A mixture of 21 g of the product of Step A and 12 g of potassium tert.-butylate in 150 ml of methanol was stirred for 2 hours at room temperature and was then evaporated to dryness. The crystals were taken up in ether, filtered and then suspended in 300 ml of acetonitrile:

17 ml of 0,0-diethyl chlorothiophosphate were added to the mixture and the mixture was refluxed for 20 hours and then was cooled. The mixture was filtered and the filtrate was evaporated to dryness. The residue was taken up in 150 ml of a 1-1 cyclohexane-ethyl acetate mixture and the mixture was vacuum filtered. The filtrate was chromatographed over silica gel and elution was with a 6–4 cyclohexane-ethyl acetate mixture to obtain 3.9 g of 2-(diethoxythiophosphoryloxy)-7-nitro-pyrido [1,2a]-pyrimidine-4-one as brown crystals melting at 94° C.

| Analysis: $C_{12}H_{14}N_3O_6PS$ | | | | |
|---|---|---|---|---|
| Calculated: | %C 40.12 | %H 3.93 | %N 11.69 | %P 8.63 |
| Found: | 40.4 | 3.9 | 11.9 | 8.6 |

Insecticidal Activity of
2-(dimethoxythiophosphoryloxy)-pyrido
[1,2a]-pyrimidine-4-one (Compound A) and
2-diethoxythiophosphoryloxy)-pyrido
[1,2a]-pyrimidine-4-one (Compound B)

A. Aphis fabae (contact ingestion)

This test used Aphis fabae and bean plants about 15 cm tall. 4 ml of an aqueous suspension of the test compounds were sprayed on each bean plant and contamination was effected with 20 wingless aphids. Two tests were run for each dose and the plants were stored at 20° C and 50% relative humidity. The percent of mortality was determined 2, 24 and 48 hours after the treatment. The results of compound A are reported in Table I as a percentage of mortality.

TABLE I

| Readings taken after hours | Dose in ppm of A | | |
|---|---|---|---|
| | 100 | 10 | 1 |
| 2 | 51 | 0 | 0 |
| 24 | 100 | 80 | 0 |
| 48 | 100 | 100 | 0 |

Table I shows that compound A has interesting insecticidal activity against Aphis fabae.

B. Test with Noctua

Prodenia litura caterpillars were used and rings having a diameter of 8 cm cut out of salad leaves were placed in sealed plastic boxes on which was placed 4 μl of an acetone solution of the test compound for each leaf ring. 15 caterpillars averaging about 10 days old were used for each test and the insects were held in natural light at 20° C and 50% relative humidity. The individuals were maintained after they had consumed the treated leaf and the percent of mortality was determined 1, 24 and 48 hours after the treatment. The results are reported in Table II for compound B.

Table II

| Readings in hours after treatment | Dose in compound B in ppm | | |
|---|---|---|---|
| | 500 | 250 | 125 |
| 1 | 0 | 0 | 0 |
| 24 | 100 | 90 | 70 |
| 48 | 100 | 100 | 80 |

Table II shows that compound B has an interesting insecticidal activity against Prodenia litura caterpillars.

C. Micro-contact on adult Musca domestica

1 μl of an acetone solution of the test product was applied with an Arnold micro applicator to the dorsal thorax of each insect previously knocked out with ether using 50 insects for each test and each concentration. The percentage of mortality of the insects was determined 24 hours after treatment and are reported in Table III.

TABLE III

| | Dose of B in ppm | | | |
|---|---|---|---|---|
| | 1000 | 500 | 250 | 100 |
| Percent mortality | 88.8 | 80.2 | 68.0 | 14.0 |

Table III shows that compound B has interesting insecticidal activity against Musca domestica.

D. Against Adult Drosophila melanogaster

To measure the activity of the vapors, insects were placed in Petri dishes connected with a tergal velum to a crystallizer of the same diameter into which is placed an acetone solution of the test product which can be evaporated before introduction of the insects. 25 adult insects less than 48 hours were used for each test and three tests were run for each concentration. The percentage of mortality was determined by comparison with untreated controls after 4 and then 24 hours. The results are in Table IV.

TABLE IV

| % mortality after hours | Concentration of B in ppm | | |
|---|---|---|---|
| | 5000 | 500 | 50 |
| 4 | 10.6 | 6.7 | 0 |
| 24 | 100 | 54.2 | 17.9 |

Test IV shows that compound B has interesting insecticidal activity against Drosophila melanogaster.

E. Against cockroaches

Cockroaches were selected by the criteria of their length and received a μl of an acetone solution of compound B between the second and third pairs of feet and after treatment, the insects were held penumbral at 20° C and the percent of mortality was determined 24 and 48 hours and 5 days after the treatment. The results are in Table V.

TABLE V

| % Mortality after | Concentration of B in ppm | | | |
|---|---|---|---|---|
| | 1250 | 1000 | 750 | 500 |
| 24 hours | 95 | 95 | 90 | 70 |
| 48 hours | 95 | 100 | 95 | 70 |
| 5 days | 100 | 100 | 100 | 95 |

Table V shows that compound B has interesting insecticidal activity against cockroaches.

F. Against Sitophilus granarius 0.2 μl of an acetone solution of the test product was placed on the ventral thorax of each of 50 insects for each concentration and the insects were kept at 20° C. The percent of mortality as compared to untreated controls was determined after 24 and 48 hours and 5 days. The results are reported in Table VI.

TABLE VI

| % Mortality after | Concentration of B in ppm | |
|---|---|---|
| | 5000 | 500 |
| 24 hours | 100 | 86 |
| 48 hours | 100 | 96 |
| 5 days | 100 | 94 |

Table VI shows that compound B has interesting insecticidal activity against Sitophilus granarius.

G. Against Tribolium confusum

The test was similar to the topical application used in Test F and the percent mortality was determined after 5 days. The results are reported in Table VII.

TABLE VII

| % Mortality after 5 days | Concentration of B in ppm | | |
|---|---|---|---|
| | 5000 | 500 | 100 |
| | 98.0 | 70.2 | 12.2 |

Table VII shows that compound B has interesting insecticidal activity against Tribolium condusum.

H. Against Carpocapsa pomonella

The test utilized a spray of 5 ml of an aqueous solution of the test product on each apple using 10 apples per concentration of 1500 or 750 ppm of compound B. On each apple, there were placed 10 to 15 eggs of Carpocapsa pomonella ready to hatch and evaluation was made after 14 days of the number of undamaged fruit. It was ascertained that at the doses used, the fruit was undamaged and compound B has an interesting insecticidal activity against *Carpocapsa pomonella*.

1. Against adult *Ceratitis capitata*

Each Orange in this test received a spray of 3 ml of an aqueous solution of compound B using two oranges at a concentration of 1000 ppm of compound B. Infestation was effected with 100 insects and the number of dead insects was determined after 2, 24 and 48 hours and 5 days. The percentage of mortality is reported in Table VIII.

TABLE VIII

| Time After | % Mortality |
|---|---|
| 2 hours | 7.2 |
| 24 hours | 28.8 |
| 48 hours | 81.4 |
| 5 days | 100 |

Compound B as seen from Table VIII has an interesting insecticidal activity against *Ceratitis capitata*.

NEMATOCIDAL ACTIVITY

The nematocidical activity of compound B was determined with dirt infested with Meloidogyne S.p.p. placed in plastic sacks with a volume of about 3 liters. Nematocidal treatment was considered efficacious at a depth of 30 cm, a volume of 3 liters of dirt corresponding to a surface of 100 $^{cm-2}$ or $10^{-6}$ ha ($100^{cm-2} \times 30$ cm = 3000 cc or 3 liters). Each volume of infested dirt received 100 ml of an aqueous suspension containing 0.250 g of compound B = to 250 Kg/ha. The controls received 100 ml of water and the plastic sacks containing the dirt were sealed immediately after treatment and then stirred in a manner to obtain a good distribution of the product. Two weeks after the treatment, the sacks were opened and the dirt was used to plant St. Pierre tomato plants in different pots. 2 months after the planting, the number of galls existing on the roots were counted and there existed in effect a relation between the population of Meloidogynes in each pot and the number of galls. The results are reported for compound B as compared to controls in Table IX.

TABLE IX

| Dose in Kg/ha | Total Galls | Average Galls per plant | Average No. of galls per g of roots | Average Weight of plants | % effici- tive |
|---|---|---|---|---|---|
| 250 | 0 | 0 | 0 | 3.7 g | 100 |
| 25 | 247 | 20.5 | 31.9 | 4.34 g | 37.4 |
| 0 | 308 | 30.8 | 51 | 5.04 g | 0 |

Compound B has a good nematocidal activity against *Meloidogyne S.p.p.*

ACARICIDAL ACTIVITY

A. Ovicide Test

Bean leaves were infested with 10 female *Tetranychus urticae* per leaf and had a coating of glue about its perimeter. The females were left for 24 hours and then were removed from the leaves. The infested leaves were divided into 2 groups: (a) the first group was treated with a spray of 2.5 ml of an aqueous solution of compound B for each leaf at a concentration of 50 or 10 mg per liter while using 4 leaves for each concentration and (b) the second control group was untreated. The number of eggs living was determined 9 days after the treatment and the results expressed as percent mortality of the eggs are reported in Table X.

TABLE X

| Dose of compound B in mg/l | % Mortality |
|---|---|
| 50 | 100 |
| 10 | 28.5 |
| 0 | 2.6 |

B. Adulticide Test

Bean leaves were infested with 25 adult *Tetranychus urticae* per leaf with glue about its periphery. The infested leaves were divided into 3 groups: (a) The first 2 groups being sprayed with 2.5 ml of an aqueous solution of either compound A or B at a concentration of 10, 1 or 0.1 mg per liter with 4 leaves being used for each concentration and (b) the third control group was untreated. The number of acarids living 48 hours after the spray was determined. The percent of mortality is reported in Table XI.

TABLE XI

| Dose of compound in mg/l | % Mortality |
|---|---|
| A - 10 | 99 |
| A - 1 | 36 |
| A - 0.1 | 7 |
| B - 10 | 100 |
| B - 1 | 46 |
| B - 0.1 | 6 |
| Control | 4 |

Tables X and XI show that compounds A and B have interesting acaricidal activity.

Various modifications of the products and process of the invention may be made without departing from the spirit or scope thereof and it is to be understood that the invention is to be limited only as defined in the appended claims.

We claim:

1. An insecticidal and acaricidal composition comprising an insecticidally and acaricidally effective amount of at least one compound of the formula

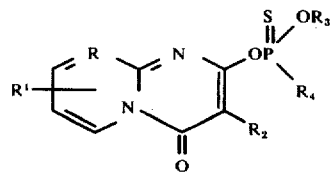

wherein R is methine, $R^1$ is selected from the group consisting of hydrogen, alkyl of 1 to 3 carbon atoms and $NO_2$, $R_2$ is selected from the group consisting of hydrogen, straight or branched alkyl of 1 to 3 carbon atoms, chlorine, bromine and alkoxycarbonyl of 2 to 4 carbon atoms, $R_3$ is branched or straight chain alkyl of 1 to 3 carbon atoms and $R_4$ is alkoxy of 1 to 3 carbon atoms and a carrier.

2. A method of combatting insect and acarid pests comprising contacting said pests with a lethal amount of at least one compound of the formula

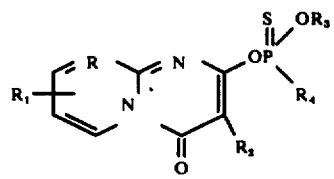

wherein R is methine, $R^1$ is selected from the group consisting of hydrogen, alkyl of 1 to 3 carbon atoms and $NO_2$, $R_2$ is selected from the group consisting of hydrogen, straight or branched alkyl of 1 to 3 carbon atoms, chlorine, bromine and alkoxycarbonyl of 2 to 4 carbon atoms, $R_3$ is branched or straight chain alkyl of 1 to 3 carbon atoms and $R_4$ is alkoxy of 1 to 3 carbon atoms.

3. A method of combatting insects comprising contacting said insects with an insecticidally efective amount of at least one compound of the formula

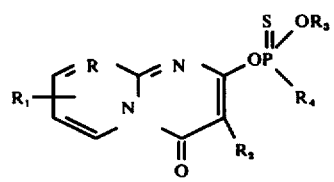

wherein R is methine, $R^1$ is selected from the group consisting of hydrogen, alkyl of 1 to 3 carbon atoms and $NO_2$, $R_2$ is selected from the group consisting of hydrogen, straight or branched alkyl of 1 to 3 carbon atoms, chlorine, bromine and alkoxycarbonyl of 2 to 4 carbon atoms, $R_3$ is branched or straight chain alkyl of 1 to 3 carbon atoms and $R_4$ is alkoxy of 1 to 3 carbon atoms.

4. A method of combatting acarids comprising contacting said acarids with an acaricidally effective amount of at least one compound of the formula

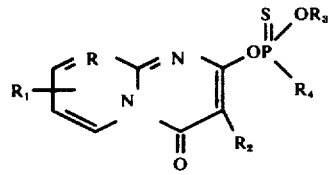

wherein R is methine, $R^1$ is selected from the group consisting of hydrogen, alkyl of 1 to 3 carbon atoms and $NO_2$, $R_2$ is selected from the group consisting of hydrogen, straight or branched alkyl of 1 to 3 carbon atoms, chlorine, bromine and alkoxycarbonyl of 2 to 4 carbon atoms, $R_3$ is branched or straight chain alkyl of 1 to 3 carbon atoms and $R_4$ is alkoxy of 1 to 3 carbon atoms.

5. A method of combatting insect and acarid pests comprising contacting said pests with a lethal amount of 2-(dimethoxythiophosphoryloxy)-pyrido [1,2a]-pyrimidine-4-one.

6. A method of combatting insects comprising contacting said insects with an insecticidally effective amount of 2-(dimethoxythiophosphoryloxy)-pyrido [1,2a]-pyrimidine-4-one.

* * * * *